(12) United States Patent
Vasilyev et al.

(10) Patent No.: US 8,278,937 B2
(45) Date of Patent: Oct. 2, 2012

(54) HIGH SPEED DETECTION OF SHUNT DEFECTS IN PHOTOVOLTAIC AND OPTOELECTRONIC DEVICES

(75) Inventors: Leonid A. Vasilyev, Beaverton, OR (US); John M. Schmidt, Oakland, CA (US); James E. Hudson, Portland, OR (US); Gregory S. Horner, Felton, CA (US)

(73) Assignee: Tau Science Corporation, Felton, CA (US)

( * ) Notice: Subject to any disclaimer, the term of this patent is extended or adjusted under 35 U.S.C. 154(b) by 426 days.

(21) Appl. No.: 12/658,489

(22) Filed: Feb. 8, 2010

(65) Prior Publication Data
US 2010/0201374 A1    Aug. 12, 2010

Related U.S. Application Data

(60) Provisional application No. 61/150,737, filed on Feb. 7, 2009.

(51) Int. Cl.
*G01R 31/02* (2006.01)
(52) U.S. Cl. ........................... 324/537; 324/555
(58) Field of Classification Search .................. 324/537, 324/555
See application file for complete search history.

(56) References Cited

U.S. PATENT DOCUMENTS

| 4,166,918 | A |   | 9/1979  | Nostrand et al. |
|-----------|---|---|---------|-----------------|
| 4,301,409 | A | * | 11/1981 | Miller et al. ............ 324/537 |
| 4,543,171 | A |   | 9/1985  | Fierster et al. |
| 4,640,002 | A |   | 2/1987  | Phillips et al. |
| 4,749,454 | A |   | 6/1988  | Arya et al. |
| 6,225,640 | B1|   | 5/2001  | Glenn et al. |

* cited by examiner

*Primary Examiner* — Vincent Q Nguyen
(74) *Attorney, Agent, or Firm* — Lumen Patent Firm

(57) ABSTRACT

The current invention provides a shunt defect detection device that includes a device under test (DUT) that is fixedly held by a thermally isolating mount, a power source disposed to provide a directional bias condition to the DUT, a probe disposed to provide a localized power to the DUT from the power source, an emission detector disposed to measure a temporal emission from the DUT when in the directional bias condition, where the measured temporal emission is output as temporal data from the emission detector to a suitably programmed computer that uses the temporal data to determine a heating rate of the DUT and is disposed to estimate an overheat risk level of the DUT, where an output from the computer designates the DUT a pass status, an uncertain status, a fail status or a process to bin status according to the overheat risk level.

23 Claims, 5 Drawing Sheets

HIGH SPEED DETECTION OF SHUNT DEFECTS IN PHOTOVOLTAIC AND OPTOELECTRONIC DEVICES

CROSS-REFERENCE TO RELATED APPLICATIONS

This application is cross-referenced to and claims the benefit from U.S. Provisional Application 61/150,737 filed Feb. 7, 2009, which is hereby incorporated by reference.

FIELD OF THE INVENTION

The invention relates to detecting defects in optoelectronics. In particular, the invention relates to a method of high-speed imaging to detect critical shunt defects in photovoltaic cells and optoelectronics in manufacturing facilities.

BACKGROUND

Photovoltaic devices regularly exhibit performance degradation due to the presence of current shunts. These shunts may be induced at various points in the process, such as problems with initial crystalline quality, contact over-firing, surface conduction at crack boundaries, trace metal deposition at the wafer edge, etc. The resultant defect population usually causes a relatively minor overall degradation of performance of a device that is properly characterized and accounted for during the final test and sort. It is important to continuously reduce the shunt defect population to improve end-of-line yield and move more cells to higher performance bins, but a more significant effect must also be considered that involves long term field reliability.

Inline shunt detection becomes particularly important when one considers the effect of reverse-bias induced shading on modules installed in the field. In the extreme case a single cell is shaded by a branch, bird or other object for some period of time and the cell is placed into strong reverse bias by its series-connected neighbors. It is not unusual for a conventional 150 mm silicon cell to be reverse-biased to more than 10V, and flow 5 A of current during the time that it is shaded. Many cells are able to survive the reverse bias condition without damage, but others experience some degree of damage as described below.

A conventional silicon cell which exhibits reasonable reverse bias current density uniformity will usually exhibit no measurable damage during the stress period. In this case, the heat load is well distributed across the cell and there is only a mild rise in local cell surface temperature. Cells that contain extensive networks of relatively small shunts may avoid degradation during reverse bias operation, where a large but well-distributed defect density effectively uses the surrounding silicon as a temperature sink to prevent local overheating. This type of cell may exhibit relatively poor efficiency at end of line test due to the network of shunts, but it will not suffer from further degradation due to the shade-induced field degradation mechanism.

Conversely, a cell with similar performance and J-V characteristics as the cell described above may be damaged if the shunts are concentrated in a localized area, or if the shunt defects are large. In this case, the entire 5 A of reverse bias current flows through a smaller area of silicon, and the higher current density (expressed in Amps/cm$^2$) may cause a local temperature rise that damages the cell within seconds. Contact de-lamination, discoloration due to transparent conductive oxide (TCO) damage, and melting of encapsulation layers are all readily observed on a variety of commercial cells, both conventional silicon and thin film, due to this effect. The localized heating may also compromise the module lamination layer, allowing moisture to enter the cell and cause freeze/thaw damage or accelerated corrosion. This damage often results in permanent degradation of cell properties: the cell no longer performs per the original J-V test results, and because the cell is series-connected in the module, the module efficiency is proportionally reduced. A similar effect occurs in thin-film cells which are monolithically grown and scribed into series-connected cells: partial shading may reverse bias one cell and cause overheating in regions where severe shunts exist. Thin-film cells often have even poorer thermal conduction characteristics than traditional bulk photovoltaic materials, and so may be more susceptible to this type of field degradation mechanism than the first generation of cells.

Cell degradation due to localized heating described above has been known for some time, but is becoming increasingly important due to the trend toward utility-scale PV contracts and purchase agreements. In years past, the predominant PV customers (homeowners) were unlikely to detect a moderate decrease of module performance year over year. Modern utility-scale installations, however, depend on Power Purchase Agreements (PPA's) that specify the precise power output of each module. New technologies are being developed to monitor the power output of every module (and in some cases even sub-module) so that the PPA's can be effectively enforced.

When PPA's are in effect, cell manufacturers benefit financially if aggressive performance guarantees can be signed, and are penalized when modules fail to meet the long-term performance goals in the field. Both parties benefit when field degradation mechanisms are controlled and eliminated.

Due to the Severity of the shading-induced mechanism discussed here, what is needed is an inline-screening test to detect cells exhibiting spatially non-uniform current flow. The solution must have high throughput (15 cells per minute or faster), must characterize the entire cell (full wafer imaging) and should be cost effective if it is to be used as an inline inspection step in the manufacturing line.

SUMMARY OF THE INVENTION

The present invention provides a shunt defect detection device that includes a device under test (DUT) that is fixedly held by a thermally isolating mount, a power source disposed to provide a directional bias condition to the DUT, a probe disposed to provide a localized power to the DUT from the power source, an emission detector disposed to measure a temporal emission from the DUT when in the directional bias condition, where the measured temporal emission is output as temporal data from the emission detector. The shunt defect detection device further includes a suitably programmed computer that uses the temporal data from the emission detector to determine a heating rate of the DUT and disposed to estimate an overheat risk level of the DUT, where an output from the computer designates the DUT a pass status, an uncertain status, a fail status or a process to bin status according to the overheat risk level.

In one aspect of the invention, the emission detector can include a photovoltaic cell, a photodiode, a thermopile detector, a microbolometer detector, a CCD camera, a CMOS camera, a thermocouple, or a thermistor, wherein operation of the DUT is stimulated with electric current in a directional bias condition and the emission is monitored.

In another aspect of the invention, the directional bias condition can be a reverse bias condition or a forward bias condition.

In a further aspect, the DUT can include at least one solar cell, at least one photo detector, at least one CCD, at least one CMOS imaging device, at least one LED, at least one solid state laser or an organometallic optoelectronic device.

According to another aspect, the emission includes light emission having a wavelength in a range of 0.4 µm to 20 µm.

In yet another aspect of the invention, the temporal data can include a time range of 0.01 to 1,200 seconds.

According to a further aspect of the invention, the power is modulated.

In one aspect, the probe provides a fixed current with compliant voltage or a fixed voltage with compliant current or a fixed power to the DUT.

In a further aspect of the invention, the thermal isolation mount can include at least one vertical suspension pin disposed between a base plate and the DUT.

According to one aspect of the invention, the defect detection device further includes a control sample, where the control sample provides at least one calibration temperature according to at least one control sample material for measuring at least one material temperature of the DUT.

In one aspect of the invention, the probe includes a mechanical positioning apparatus, where the probe can be positioned to a precision in a range of 10 µm to 2 mm.

In a further aspect, the overheat risk level can include parameters such as DUT capacitance, time rate of change of temperature, temperature, I-V characteristics, light emission detected by a camera as a function of the electrical bias applied to the DUT, a surface temperature measured by a camera as a function of a directional electrical bias applied to the DUT, where the directional electrical bias can include voltage and current waveforms, a spatial pattern of light emission detected by the camera during a reverse bias operation of the DUT, a spatial pattern of light emission detected by the camera during a forward bias operation of the DUT, a surface temperature measured by the camera as a function of time under conditions of applied voltage or current.

In yet another aspect of the invention, the emission detector can include a translating mount having positioning increments in the range of 0.05 mm to 10 mm.

In a further aspect, the emission detector can include a goniometer to point the heat detector at different regions of the DUT.

In a further aspect, the emission detector has a detection sensitivity in an energy region of at least one bandgap of the DUT.

In another aspect of the invention, the emission can include an emission frequency or an emission intensity, where the emission enables determination of a quality of the DUT or contamination patterns of the DUT.

According to another aspect, a second electroluminescence detection camera is disposed to detect band-to-band or impurity-assisted luminescence, where electroluminescent patterns are characterized with the thermal emission of the DUT.

According to one aspect, a spatial emissivity variation of the DUT is compensated for by applying a correction factor on a pixel-by-pixel basis, where an overheating potential of the DUT is determined.

In another aspect of the invention, determined temperature variations of the DUT are addressed and uniquely analyzed on a pixel-by-pixel basis to provide increased sensitivity at critical locations in the DUT.

In a further aspect, determined temperature variations of the DUT are addressed on a pixel-by-pixel basis to correct for known heatsink effects from an underlying or overlying sample holder.

According to one aspect of the invention, the shunt defect detection device further includes an I-V tester that is disposed to measure cell current output, voltage, shunt resistance, series resistance, conversion efficiency and fill factor, where the DUT is appropriately binned, according to the criteria of a DUT manufacturer.

In yet another aspect of the invention, the DUT is automatically transferred to a pass, an uncertain bin, a fail bin, or a further testing bin according to the output status.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Figure 1:
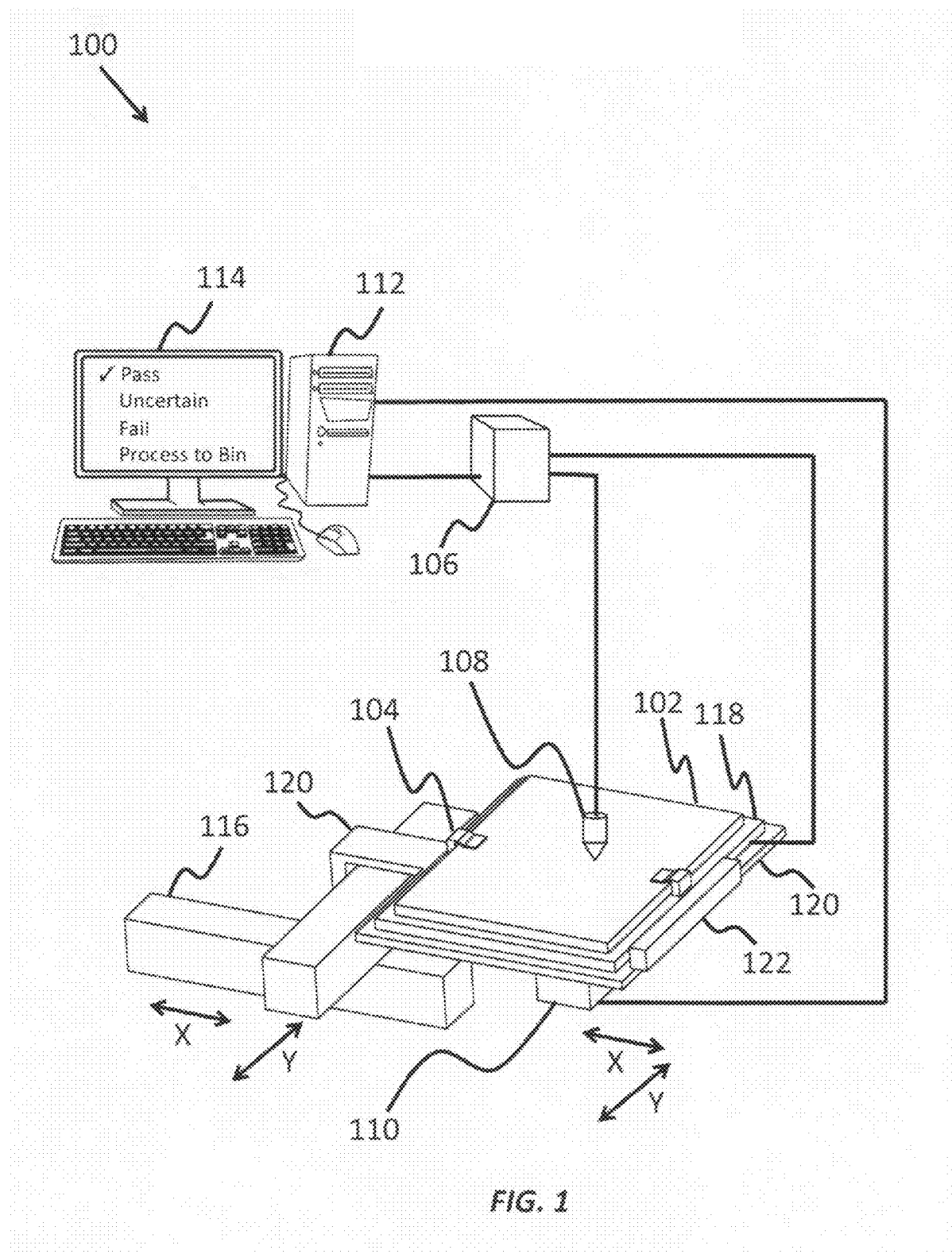
FIG. 1 shows a schematic drawing of the shunt defect detection device according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

According to the current invention, a solar cell, also known as a photovoltaic cell, is a device capable of absorbing incoming sunlight (photons) and delivering electric power to an external load. Photovoltaic cells are provided in many forms that include Copper Indium Gallium Diselenide (CIGS), amorphous silicon (a-Si) and Cadmium Telluride (CdTe), which are typical thin-film solar cell materials, and crystalline silicon (x-Si), a type of (usually) thick-film (either single-crystal or poly-crystal) material used in traditional solar cells.

In this application, a camera is any device capable of forming a one-dimensional or two-dimensional image from measurements of infrared radiation flux. For instance, a camera may be constructed from a two-dimensional array of infrared sensors, or it may be constructed from a single sensor with a moving optic component that is able to scan the sample area and record a two-dimensional image from the recorded data set. Further, the camera may be constructed from a one-dimensional array of infrared sensors, and either the sample or the camera may be scanned in at least one direction to construct a two-dimensional image of the infrared emission. In general, the term 'infrared' shall be used to indicate the wavelengths of radiation from 700 nm to 1 mm, or a sub-region thereof, and the visible spectrum can include 350 nm to 700 nm.

The current invention is directed toward shunt detection in a device under test (DUT), where a shunt is a type of localized defect in photovoltaic solar cells which allows current to flow through the device when a voltage bias is applied, the defect acts in parallel with the desired P-N junction behavior, and thus limits the output current of the device. This current flow is undesirable because it decreases the device efficiency and may eventually cause damage to the device if localized overheating occurs from excessive current density at the location of the shunt defect.

In this application, the term DUT may be any of the following:
- A single solar cell
- A collection of solar cells, connected in series, parallel, or a combination of the two. This collection may represent a manufacturer's 'module', a collection of modules, or a subset of cells within the module.
- A single, monolithically grown solar cell module (such as a-Si on glass substrate or CIGS on steel)
- A photodetector element or array
- A photodiode element or array
- A Charge Coupled Device (CCD) element or array
- A Light Emitting Diode (LED) element or array
- A Solid State Laser element or array
- Organometallic optoelectronic devices.

The current invention provides shunt defects detection in optoelectronic devices (photovoltaic cells, light emitting diodes, photodiodes, solid state lasers, etc.) by stimulating the device with electric current and monitoring the emitted light. The invention detects the light emitted from photovoltaic solar cells that are stimulated with electrical reverse bias, where the light emitted can include infrared, visible and UV light.

Referring to the figures, FIG. 1 shows a schematic drawing of the shunt defect detection device 100 according to the current invention. As shown, the shunt defect detection device 100 that includes a device under test (DUT) 102 that is fixedly held by a thermally isolating mount 104, a power source 106 disposed to provide a directional bias condition to the DUT, a probe 108 disposed to provide a localized power to the DUT 102 from the power source 106, an emission detector 110 disposed to measure a temporal emission from the DUT 102 when in the directional bias condition, where the measured temporal emission is output as temporal data from the emission detector 110. It should be apparent that the detector 110 can be mounted either above or below the DUT 102, where the optimal position is determined b the location of metal conductors in the DUT 102 that may obstruct or screen the thermal emission from the DUT 102. For example, if the back side of the DUT 102 is coated with metal, the camera (emission detector 110) can be mounted where it is disposed to view the front side of the DUT 102.

Figure 2:
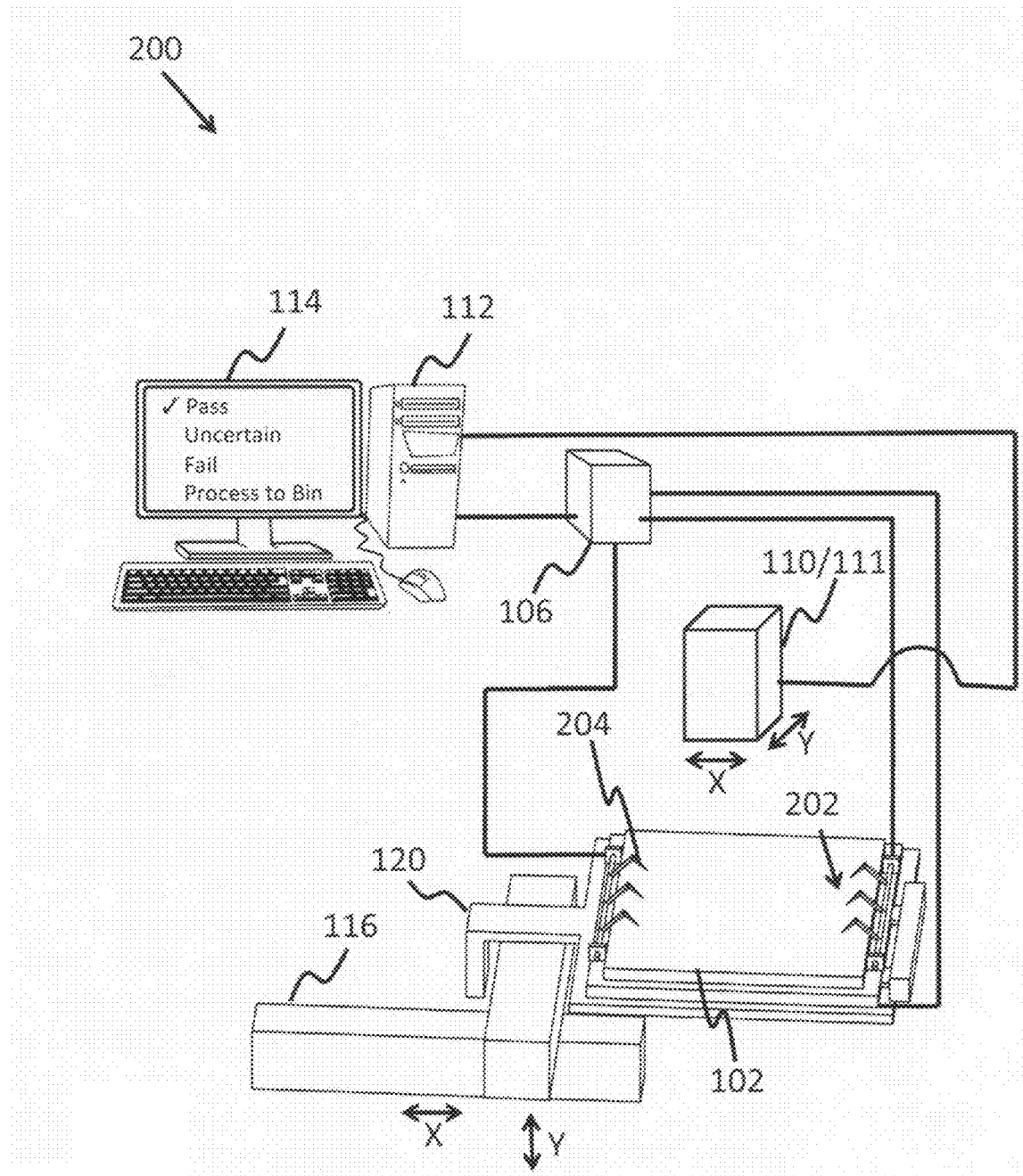
FIG. 2 shows a schematic drawing of the shunt defect detection device according to the present invention.

The shunt defect detection device further includes a suitably programmed computer 112 that uses the temporal data from the emission detector 110 to determine a heating rate of the DUT 102 and disposed to estimate an overheat risk level of the DUT, where an output 114 from the computer 112 designates the DUT 102 a pass status, an uncertain status, a fail status or a process to bin status according to the overheat risk level. Further shown in FIG. 1 is an x-y translation stage 116 and a stage-mounted frame 120 disposed to position the DUT 102 mounted to a PCB 118 over the emission detector 110 when a directional bias is applied through the probe 108. Additionally, the defect detection device 100 further includes a control sample 122, where the control sample 122 provides at least one calibration temperature according to at least one control sample material for measuring at least one material temperature of the DUT 102. In FIG. 1 and FIG. 2, a software interface 114 is provided to allow the user to select from a plurality of algorithms and control limits and recalculate Pass/Fail results from archived data sets so that the user can assess the results of various algorithms and control limits on statistical process control data. Further, the software program can be disposed to plot 'Pass', 'Fail', and 'Inconclusive' results as a function of time, sample ID, sample type, substrate batch, substrate vendor, shift, and/or operator, as well as other parameters that may be used to sort data such as the identity of upstream processing equipment (Furnace ID, etc.) used to create a given cell, or processing parameters (Furnace temperature, etc.) used during the processing of a given cell. Additionally the software program can be disposed to use time, sample ID, sample type, substrate batch, substrate vendor, shift, operator, identity of upstream processing equipment (Furnace ID, etc.), and/or processing parameters (Furnace temperature, etc.) to correlate and suggest potential causes of 'Failed' samples. Further, the software program can be disposed to calculate a parameter, here named 'severity', used to characterize the overheating potential of the sample. Here, the severity parameter is used to characterize the overheating potential of the sample, which is derived from a mathematical analysis of one or a combination of the following parameters:
- The light emission detected by a camera as a function of the electrical bias [voltage and current waveforms] applied to the DUT.
- The surface temperature measured by the Camera as a function of the electrical bias [voltage and current waveforms] applied to the DUT.
- The measured cell capacitance.
- The spatial pattern of visible or infrared emission detected by the Camera during reverse bias operation of the DUT.
- The spatial pattern of visible or infrared emission detected by the Camera during forward bias operation of the DUT.
- The surface temperature measured by the Camera as a function of time under specific conditions of applied voltage or current.

In one aspect of implementation, the DUT 102 is assembled in advance to the PCB 118 using the thermally isolated mounts 104 and is placed on the stage-mounted frame 120 for rapid processing. This process may be automated or accomplished manually.

It should be obvious to one skilled in the art that the emission detector 110 may also be disposed on a translation stage 116 to enable greater measurement flexibility.

FIG. 2 shows an alternate embodiment 200 of the current invention, where shown are mounting probes 202 disposed to fixedly hold the DUT 102 in addition to provide the localized directional bias through a probe tip 204. A more detailed discussion of the mounting probe 202 is provided in FIGS. 3a-3c.

In one aspect, the emission detector 110 can be one or more thermopile detectors to measure the infrared light emitted from a DUT 102 during or soon after the application of reverse bias condition to the device. Further, the emission detector 100 can be one or more microbolometer detectors to measure the infrared light emitted from a DUT 102 during or soon after the application of the directional bias condition, for example a reverse bias condition, to the device. The invention can measure the infrared emission from the DUT 102 as a function of time and analyzes the resulting dataset to predict the risk that the device will overheat during field operation. In one aspect, the invention acquires only a small amount of data [typically 0.1 to 10 seconds] and uses a model-based curve-fitting algorithm to extrapolate the predicted temperature vs. time.

According to one embodiment, the invention includes a controller (computer 112 or circuitry) to coordinate a test sequence, a power supply 106 or amplifier having >0.05 Hz frequency response. In the preferred embodiment, a frequency response of 10-5000 Hz is used. The current embodiment further includes a probe mechanism 108/202 that is able to make electrical contact to the DUT 102 either automatically or with the assistance of an operator, and deliver current to the DUT 102 through the probes 108/202. As an example, one could use a current or voltage source with an electrical switch connected between the DUT 102 and the source 106. The emission detector 110 can further include a camera or an array of cameras to measure the surface temperature of the DUT 102 during the test sequence. Here, the camera can include one or more thermopile detectors, or one or more microbolometers, or one or more infrared-sensitive photodetectors. In one aspect of the current embodiment, the surface temperature can be measured by an array of thermocouples or thermistors held either in contact with or in close proximity to the surface of the DUT. The sufficiently programmed computer 112 includes an algorithm that controls the test sequence and conditions that are applied to the DUT 102, where the test sequence may be specified in terms of the timing of applied current and/or applied voltage. Further, the invention can include an algorithm that collects the sequence of infrared data from the camera and mathematically characterizes or predicts the overheating potential (here named 'severity') of the DUT 102. In one aspect the algorithm uses the measured infrared characteristics as a function of time to predict the overheating severity in approximately one second, or uses the measured infrared characteristics as a function of time, and dynamically adjusts the length of the test until a conclusive result is determined, or a timeout period has been reached.

According to one embodiment, the sufficiently programmed computer 112 allows a user to store, analyze and review previously acquired data and results.

In one aspect of the invention, a machine-vision system is disposed to manually or automatically position electrical contacts in the proper locations prior to the start of the test.

According to one aspect of the invention, the shunt defect detection device 200 replaces the top emission detector 110 with an I-V tester 111 (shown on the top of the DUT 102), where the bottom emission detector 110 of FIG. 1 remains in place and the shunt defect detection device 200 has an I-V tester 111 that is disposed to measure cell current output, voltage, shunt resistance, series resistance, conversion efficiency and fill factor, where the DUT 102 is appropriately binned, according to the criteria of a DUT 102 manufacturer.

In a further aspect, and in a similar configure as above, a second electroluminescence detection camera 110 is disposed to detect band-to-band or impurity-assisted luminescence, where electroluminescent patterns are characterized with the thermal emission of the DUT 102.

Figure 3:
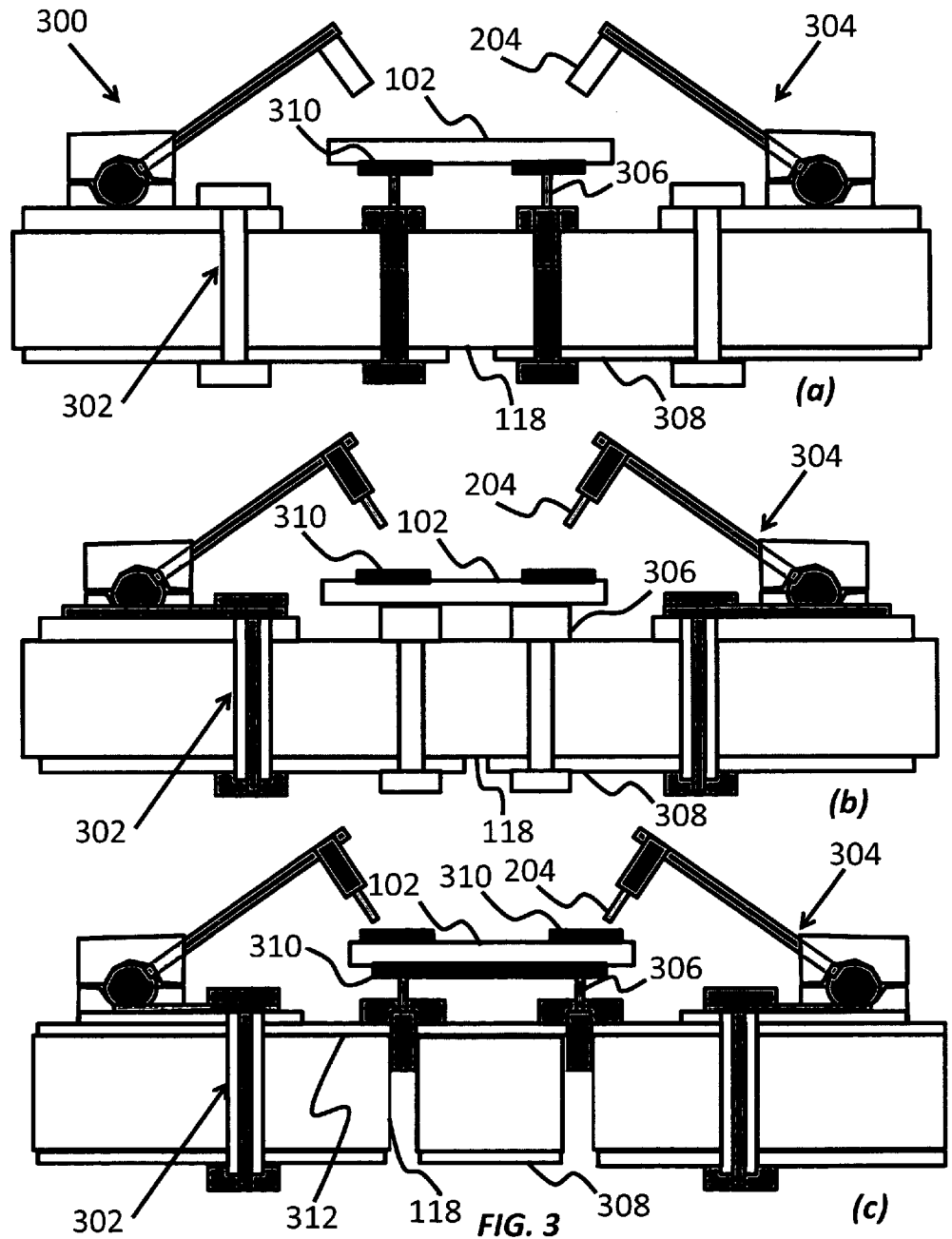
FIGS. 3a-3c show variations to the mounting probes according to the present invention.

FIGS. 3a-3c show mounting probes variations 300 according to the present invention, where, shown are a PCB 118 with through-hole vias 302, and a rotating shaft 304 mounted to a top surface of the PCB 118. The rotating shaft 304 may be conductive, or an insulating shaft with individual wires routed to the end of the probe tip 204, and the probe tip 204 may also be conductive or insulating depending on the desired configuration described below. DUT's 102 generally have two types of contacts (positive and negative polarity) per pn junction, and these may be arranged a) separately on front and back of the DUT 102, b) both on front, c) both on back. The mounting probe 204 and DUT 102 support apparatus is configurable to make electrical contact to front and back contacts, as needed, while simultaneously minimizing thermal conductance to and from the DUT 102. Referring to FIG. 3a, the mounting probe tip 204 and the rotating shaft 304 are electrically insulated and the DUT 102 is disposed on a support pin 306 that is conductive and electrically connected through a via 302 to a bottom conductive surface 308 on the PCB 118, where the shaded regions represent conducting material and the non-shaded regions through the vias 302 and with some support pins 306 represent insulating material. The insulating probe tip 204 rotates down to the DUT 102 to hold it in place, while the conductive pin 306 provides one polarity of bias to the DUT 102. The second polarity will be delivered to a separate region of the DUT 102, and use a separate backplane to isolate the signal polarities. A conductive DUT region 310 is shown on the bottom surface of the DUT 102 that is connected to one terminal of the controller 106 and a separate region of the bottom conductive surface 308 on the PCB 118 is connected to another terminal of the controller 106 to provide the directional bias for shunt detection.

FIG. 3b shows a conductive mounting probe tip 204 and the rotating shaft 304 are conductively connected a to bottom conductive surface 308 on the PCB 118 and the support pin 306 is insulating. The conductive probe tip 204 rotates down to the DUT 102 to make electrical contact and to hold it in place. A conductive DUT region 310 is shown on the top surface of the DUT 102 that is connected to one terminal of the controller 106 and the bottom conductive surface 308 on the PCB 118. A second probe, identical in function to probe tip 204, provides a second electrical contact to the front of the DUT 102, and is connected to another terminal of the controller 106 to provide the directional bias for shunt detection. An insulating support pin 306 may be inserted to elevate the DUT 102 to reduce heatflow between the DUT 102 and the PCB or underlying support structure.

FIG. 3c shows a conductive mounting probe tip 204 and the rotating shaft 304 are conductively connected to a bottom conductive surface 308 on the PCB 118. The support pin 306 is a press-fit pin that is also conducting and is conductively connected to a top conductive surface 312 on the PCB 118. The conductive probe tip 204 rotates down to the DUT 102 to hold it in place. After rotation, electrical contact is made between DUT surface contact 310 and probe tip 204, where the conductive probe tip 204 is connected to the bottom conductive surface 308 on the PCB 118 and one terminal of the controller 106. A second contact is made to the back side of the DUT 102 by a conducting support pin 306, that is connected to the top conductive surface 312 and is connected to another terminal of the controller 106 to provide the directional bias for shunt detection.

The number and combination of support pins 306 and probe tips 204 can be varied according to a desired arrangement, where any combination of conducting and insulating configurations are possible without departing from the spirit of fixedly holding in a plane and forcing to be flat, the DUT 102 and providing a directional bias thereto.

Figure 4:
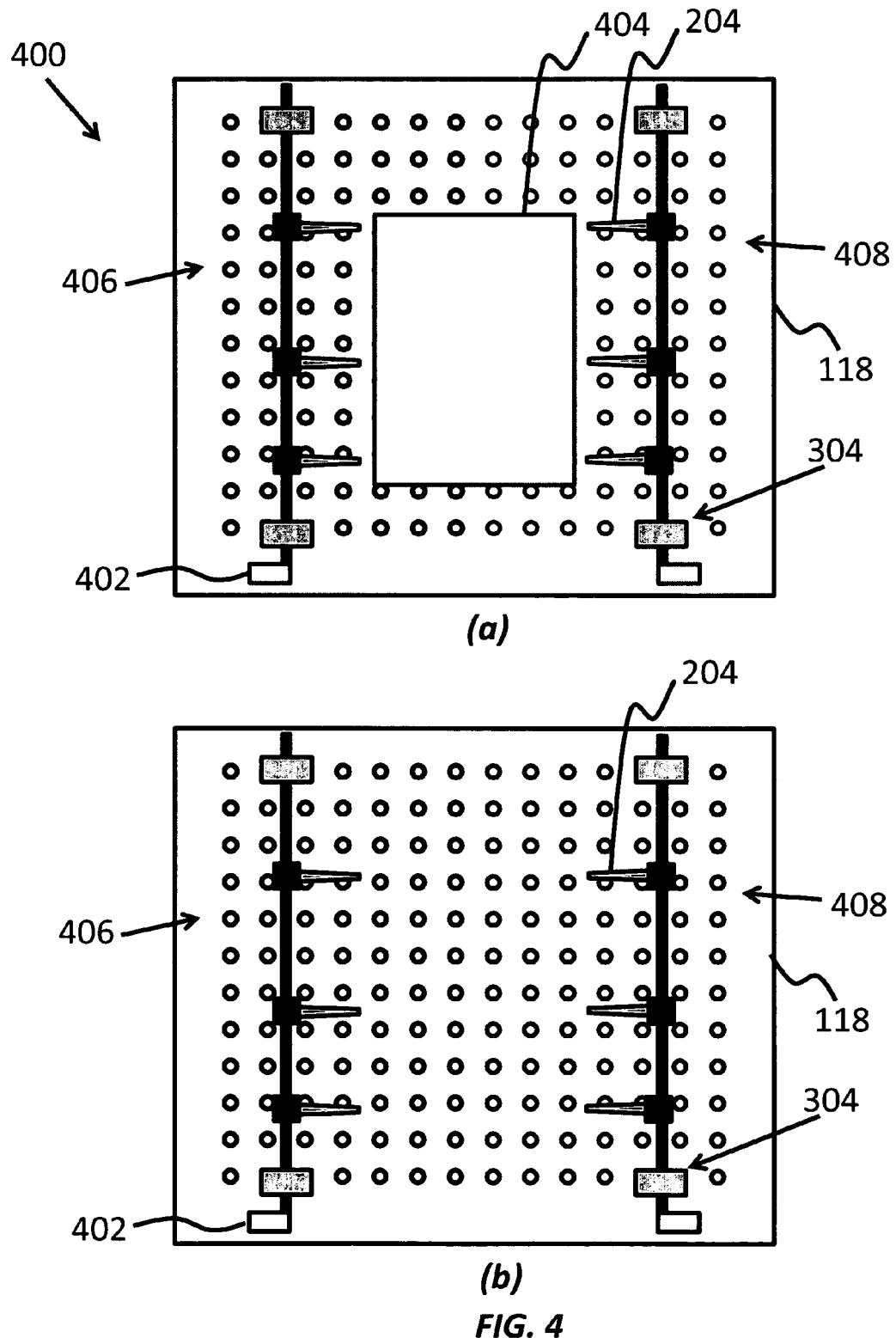
FIGS. 4a-4c show some exemplary PCB configurations according to the present invention.
Figure 4:
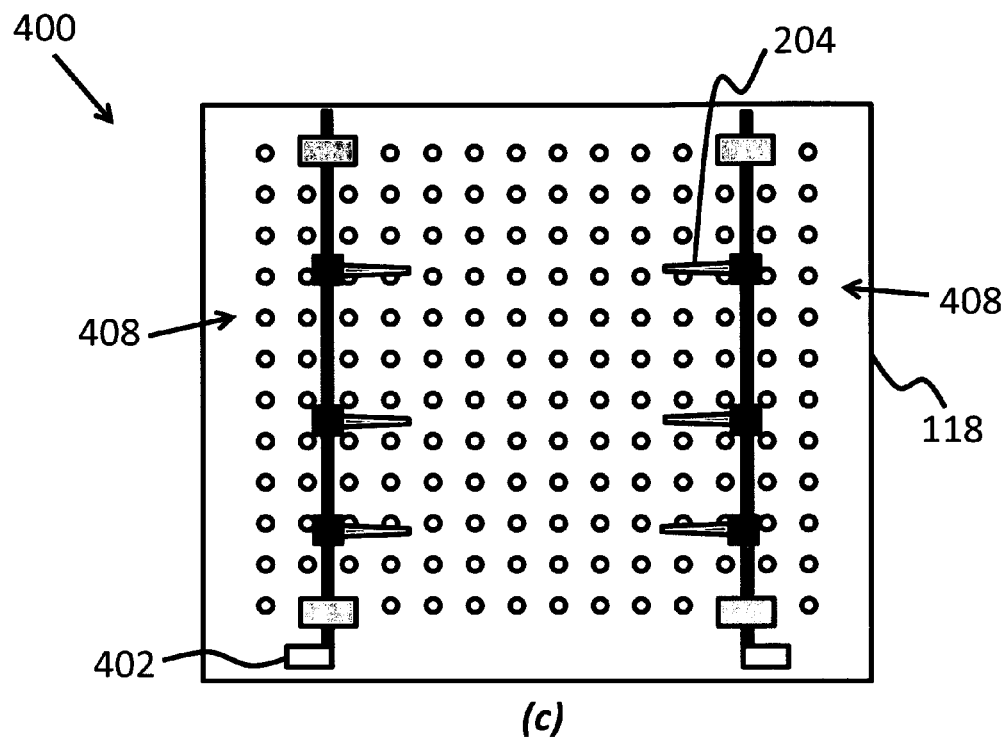

FIGS. 4a-4c show some exemplary PCB configurations 400, where shown are the rotating shafts 304 having a rotation actuator 402 that can be operated manually or automatically to position the probe tips 204. FIG. 4a shows the PCB 118 having an opening 404 for when the PCB 118 is used for transmittance evaluation of the DUT 102 (not shown). Further shown in FIGS. 4a-4b is the PCB 118 having a conductively connected set of first polarity conductive vias 406 and a conductively connected set of second polarity conductive vias 408, where the respective sets are opposite polarity. FIG. 4c shows the PCB 118 having a single conductively connected set of conductive vias 408.

The following examples are provided to further described the acquisition and use of data without limiting the scope of the current invention:

Example #1

A step function current of −6 A is applied at time T=0 seconds, and surface temperature images are recorded for a total of 1.5 seconds at intervals of 0.15 seconds. The set of surface temperature images is analyzed to determine the heating rate and/or extrapolate the maximum temperature at each pixel. The set of results from all pixels may then be processed (averaged, spatially filtered to exclude edge effects, spatially analyzed to determine the number and/or proximity of shunts, spatially analyzed to determine the rate of change (in degrees/unit length) as a function of position, binned via histogram to analyze only a portion of the pixels, etc.) to generate the final results such as 'Pass', 'Fail', 'Inconclusive', or a mathematical indicator derived from one or more of the measured parameters that indicates the overheating potential for the cell.

Example #2

A pulsed square-wave voltage waveform is applied to the DUT, with peak voltage=−10V, minimum voltage=0V, and frequency=4.5 Hz. The surface temperature image is measured at a frequency of 9 Hz, and the resultant data is analyzed to determine the heating rate and/or extrapolate the maximum temperature at each pixel. The set of results may then be processed as described in Example #1.

Example #3

A step function current of −4 A is applied at T=0 seconds, and the surface temperature is recorded for a user or algorithm defined time (e.g., 60 seconds) at intervals of 0.15 seconds. The set of surface temperature images is analyzed to find the maximum temperature over the measurement period, as well as the maximum heating rate observed during the measurement. The set of results may then be processed as described in Example #1.

According to one aspect of the invention, the current-voltage (I-V) or current density-voltage (J-V) characteristics of the cell may also be measured and used as a component of the severity calculation. For instance, cells with large reverse bias current leakage may have a higher potential for overheating than cells with low reverse bias leakage. The following example provides illustration for this aspect with limiting the scope of the invention.

Example #4

Calculate the maximum rate of heating, as described above. Multiply this by the reverse bias current (or a function of the reverse bias current) measured at −4V applied voltage. The result (e.g.—with dimensions of Amps*Celcius/sec) may be used as an indicator of the overheating Severity for solar cells.

According to another aspect of the invention, the 'Pass', 'Fail' and 'Inconclusive' control limit criteria can be expressed in the form of histograms (the histogram, in this case, is the number or percentage of pixels plotted vs. Severity) and applied to the measurement output to determine the test results. The algorithm may be used to analyze a single image or sequence of images and compare the observed histogram against the control limit histograms. In an alternate form of this method, the cumulative probability (the number or percentage of pixels with severity at and below a certain severity level) may be used as a histogram control limit. In its simplest implementation, the severity parameter is simply equal to the temperature. In a more complex implementation, the severity parameter is a function of the measured parameters described above [capacitance, time rate of change of temperature, temperature, I-V characteristics, etc.].

In a further aspect of the invention, a reference sample 122 may be designed and used to generate known surface temperatures. This sample 122 may be either manually or automatically positioned in view of the infrared camera to provide an independent temperature calibration at prescribed intervals.

In one embodiment, the reference sample 122 is a collection of resistive elements arranged into a two-dimensional array. Current is forced through each resistive element to achieve the desired power dissipation.

In another embodiment, the reference sample 122 may be pre-calibrated using a reference camera or a contacting temperature measurement (thermocouple, thermistor, etc.) so that the surface temperature of each resistive element is known as a function of current.

In a further embodiment, the reference sample 122 may include integrated temperature sensors thermally coupled to each resistor so that the surface temperature at each resistive element may be electronically read from the reference sample.

Camera calibration may be accomplished by comparing the surface temperature recorded by the infrared camera with a surface temperature from the reference sample 122. Here, the results are stored in a functional form (for example, Temp_actual=A*Temp_measured+B or a more complex functional form) or a lookup table of the measured temperature versus the actual temperature. Alternately, a separate calibration formula or lookup table may be applied to each pixel to correct for pixel-to-pixel non-uniformities in the camera. The same type of pixel-by-pixel calibration factor may be used to correct for known patterns of emissivity variation on the sample, for example, to increase the reported (measured) temperature in regions of low emissivity.

According to one aspect, a spatial emissivity variation of the DUT 102 is compensated for by applying a correction factor on a pixel-by-pixel basis, where an overheating potential of the DUT 102 is determined.

In another aspect of the invention, determined temperature variations of the DUT 102 are addressed and uniquely analyzed on a pixel-by-pixel basis to provide increased sensitivity at critical locations in the DUT 102.

In a further aspect, determined temperature variations of the DUT 02 are addressed on a pixel-by-pixel basis to correct for known heatsink effects from an underlying or overlying sample holder.

In another aspect, the invention includes a suitably programmed computer 112 having an algorithm that analyzes the set of thermal images and other parameters described above and calculates whether the DUT 102 should be 'passed', 'failed', or marked as 'inconclusive.'

During periods when the AC power supply is not within voltage, current or frequency specifications, the invention may further include an uninterruptible power supply 106 used to allow, one or more of the following:

Continuous, uninterrupted operation of the system.
A successful system shutdown of the system, which preserves all data acquired up to that point.
The successful completion of a wafer handling operation to ensure sample integrity.

In a further aspect of the invention, an enclosure is provided, which prevents stray light radiation (visible and/or infrared) from reaching the camera.

Additionally, an enclosure may be provided, which protects the user from accidental contact with the cell during test.

A camera mount may be provided, which allows the camera to be positioned at an angle so that the thermal signature of the camera is not reflected by the sample back into the camera [this prevents the warm camera sensor from 'seeing itself' in the reflection].

Further, a mount may be provided, which holds a block of material so that the image of the material is reflected by the sample into the camera. This block of material may be temperature stabilized or cooled to provide a repeatable background signal for the measurement and minimize the noise contribution of the reflected image to the total measurement.

According to one aspect of the invention, an automated or manually operated door can be disposed to allow sample loading and unloading when open, and is interlocked to prevent system operation until the door is properly closed.

In a further aspect, a stage is provided that is disposed to translate the camera or sample in x-y increments (typically 0.05-10 mm), which are smaller than the spatial resolution, measured at the plane of the sample, of a single camera pixel. A sequence of images may be acquired to construct an image with spatial resolution exceeding that of any one image. For instance, if a 30×30 element infrared camera is used to measure the surface temperature of a 150 mm×150 mm DUT, the spatial resolution at the plane of the sample is 150 mm/30=5 mm. In this case, an x-y stage may be used to translate the camera (for instance) ½ the spatial resolution (2.5 mm) in the x-direction between two images. The two images may be compared, where a single image may be calculated which has x-resolution better than either of the original images. The process may be repeated in both the x- and y-directions to achieve enhanced two-dimensional resolution. Because thermopile, microbolometer, and other presently available infrared detectors have relatively low spatial resolution, this resolution enhancement technique is important to achieve acceptable spatial resolution, according to the current application.

In one aspect, a stage is provided, similar to that described above, but is disposed to translate the sample or camera laterally by distances that exceed the dimension of the field of view. For example, the system may acquire several images at spacings selected to be nearly equal to the camera field of view, and then stitch the images together into one large image for subsequent analysis. Because thermopile, microbolometer, and other presently available infrared detectors have relatively low pixel counts, this stitching technique is important to achieve an acceptable combination of spatial resolution and field of view, according to the current application.

In a further aspect, a rocking mechanism (goniometer) is provided that is disposed to point the camera at different regions of the sample. Small rocking motions may be used to generate sub-pixel image shifts for the purpose of resolution enhancement (as described above). Large rocking motions may be used to generate image shifts on the order of a field of view for the purpose of stitching together a single image with larger field of view (as described above)

The above-described invention may be further combined with other elements, to provide the unique ability to characterize the performance of solar cells as well as the presence of shunt defects that may cause cell degradation. The other elements can include an illuminated J-V tester that is used to measure the conversion efficiency of solar cells. Other elements further include filters to modify the lamp spectra so that they better match the desired solar spectrum, a device that places probes on the appropriate region of the DUT 102 so that current output can be measured under various electrical load and illumination conditions, a mechanical sorting device that allows the combined J-V and defect tester to group samples into a discrete number of bins, based on a combination of J-V (measured conversion efficiency, current output, etc.) and defect characteristics, a temperature-controlled chuck which allows each sample to be measured at a predetermined temperature, and an enclosure which prevents users from being exposed to unsafe levels of radiation and/or unsafe electrical energy, and/or unsafe mechanical hazards.

According to a further aspect of the invention, an electroluminescence imaging system is provided that is disposed to acquire emission from the sample during forward bias (the LED operating regime) and/or reverse bias. Here, the camera used to monitor luminescence can have sensitivity in the region near the bandgap or bandgaps of the material to be monitored (for example, photon energies near 1.1 eV for x-Si, 0.7 eV for Germanium, etc.). The forward bias electroluminescence images, when analyzed vs. emission frequency or intensity, may be used to monitor sample quality and contamination patterns. These images may provide clues to the contamination source (handprints, the pattern from a robotic wafer handler, linear tracks left by assembly line rollers, etc.). The reverse bias and forward bias images may be used to provide high-resolution images of the shunt defect population. Although there are significantly fewer photons emitted by shunt defects in the short-wavelength (UV-VIS-NIR) region than in the infrared, long-duration exposures may be used with Silicon, GaAs, or other relatively short-wave detectors to provide much higher resolution images than are possible with today's thermopile or microbolometer technologies.

In a further aspect of the invention, the transfer of electronic or physical navigation information (a map of defects or features from the DUT 102) from an apparatus described above to an integrated or independent system for purposes of relocation of the feature or defect. Relocation could have, but is not limited to, use for editing the DUT 102 to remove or alter the defect or feature using a laser, a sputtering system, a chemical treatment (such as deposition, dissolution, or passivation), or any other technique which is used to directly or indirectly augment the material or electrical properties of the DUT 102. Further, relocation includes investigating properties of a defect or feature region on the DUT 102 through analysis with optical microscopes, electron microscopes, ion microscopes, chemical probes, or other analytical technique.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, these measurements may be applied to a string of DUT's already soldered together, a matrix of DUT's (an assembly of more than one string) or a completely fabricated module composed of a plurality of DUT's. As another example, the collection of emission from the DUT may be assisted with various lenses or reflective elements. As a third example, various wavelength-selective filters may be used to block unwanted emission from reaching the detector, while allowing the signal of interest to reach the detector. As a fourth example, the DUT clamping mechanism may be replaced with a conventional clamping mechanism, such as a vacuum chuck. As a fifth example, a plurality of both front and rear contact points may be used to sufficiently support the sample and provide appropriately low resistance paths to conduct the DUT current. As a sixth example, additional isolated contacts may be added to support tests of 3-terminal (or a plurality of terminals) on a device. As a seventh example, multilevel PCB's may be used to accommodate additional contacts to the device. As an eighth example, the PCB described here may be replaced with another material that provides sufficient support, and may be modified appropriately to route the appropriate currents to and from the DUT All such variations are considered to be within the scope and spirit of the present invention as defined by the following claims and their legal equivalents.

What is claimed:

1. A shunt defect detection device, comprising:
   a. a device under test (DUT), wherein said DUT is fixedly held by a thermally isolating mount;
   b. a power source, wherein said power source is disposed to provide a directional bias condition to said DUT;
   c. a probe, wherein said probe is disposed to provide a localized power to said DUT from said power source;
   d. an emission detector, wherein said emission detector is disposed to measure a temporal emission from said DUT when in said directional bias condition, wherein said measured temporal emission is output as temporal data from said emission detector; and
   e. a suitably programmed computer, wherein said suitably programmed computer uses said temporal data from said emission detector to determine a heating rate of said DUT and disposed to estimate an overheat risk level of said DUT, wherein an output from said computer designates said DUT a pass status, an uncertain status, a fail status or a process to bin status according to said overheat risk level.

2. The shunt defect detection device of claim 1, wherein said emission detector is selected from the group consisting of a photovoltaic cell, a photodiode, a thermopile detector, a microbolometer detector, a CCD camera, a CMOS camera, a thermocouple, and a thermistor, wherein operation of said DUT is stimulated with electric current in said directional bias condition and said emission is monitored.

3. The shunt defect detection device of claim 1, wherein said directional bias condition comprises a reverse bias condition or a forward bias condition.

4. The shunt defect detection device of claim 1, wherein said DUT is selected from the group consisting of at least one solar cell, at least one photo detector, at least one CCD, at least one CMOS imaging device, at least one LED, at least one solid state laser and an organometallic optoelectronic device.

5. The shunt defect detection device of claim 1, wherein said emission comprises light emission having a wavelength in a range of 0.4 μm to 20 μm.

6. The shunt defect detection device of claim 1, wherein said temporal data comprises a time range of 0.01 to 1,200 seconds.

7. The shunt defect detection device of claim 1, wherein said power is modulated.

8. The shunt defect detection device of claim 1, wherein said probe provides a fixed current with compliant voltage or a fixed voltage with compliant current or a fixed power to said DUT.

9. The shunt defect detection device of claim 1, wherein said thermal isolation mount comprises at least one vertical suspension pin disposed between a base plate and said DUT.

10. The shunt defect detection device of claim 1 further comprises a control sample, wherein said control sample provides at least one calibration temperature according to at least one control sample material for measuring at least one material temperature of said DUT.

11. The shunt defect detection device of claim 1, wherein said probe comprises a mechanical positioning apparatus, wherein said probe can be positioned to a precision in a range of 10 μm to 2 mm.

12. The shunt defect detection device of claim 1, wherein said overheat risk level comprises parameters selected from the group consisting of DUT capacitance, time rate of change of temperature, temperature, I-V characteristics, light emission detected by a camera as a function of the directional electrical bias applied to said DUT, a surface temperature measured by a camera as a function of said directional electrical bias applied to the DUT, a spatial pattern of light emission detected by said camera during a reverse bias operation of said DUT, a spatial pattern of light emission detected by said camera during a forward bias operation of said DUT, and a surface temperature measured by said camera as a function of time under conditions of applied voltage or current, wherein said directional electrical bias comprises voltage and current waveforms.

13. The shunt defect detection device of claim 12, wherein electrical bias applied to said DUT comprises voltage and current waveforms.

14. The shunt defect detection device of claim 1, wherein said emission detector comprises a translating mount having positioning increments in the range of 0.05 mm to 10 mm.

15. The shunt defect detection device of claim 1, wherein said emission detector comprises a goniometer to point the emission detector at different regions of said DUT.

16. The shunt defect detection device of claim 1, wherein said emission detector has a detection sensitivity in an energy region of at least one bandgap of said DUT.

17. The shunt defect detection device of claim 1, wherein said emission comprises an emission frequency or an emission intensity, wherein said emission enables determination of a quality of said DUT or contamination patterns of said DUT.

18. The shunt defect detection device of claim 1, wherein a second electroluminescence detection camera is disposed to detect band-to-band or impurity-assisted luminescence, wherein electroluminescent patterns are characterized with said thermal emission of said DUT.

19. The shunt defect detection device of claim 1, wherein a spatial emissivity variation of said DUT is compensated for by applying a correction factor on a pixel-by-pixel basis, wherein an overheating potential of said DUT is determined.

20. The shunt defect detection device of claim 1, wherein determined temperature variations of said DUT are addressed and uniquely analyzed on a pixel-by-pixel basis to provide increased sensitivity at critical locations in said DUT.

21. The shunt defect detection device of claim 1, wherein determined temperature variations of said DUT are addressed on a pixel-by-pixel basis to correct for known heatsink effects from an underlying or overlying sample holder.

22. The shunt defect detection device of claim 1 further comprises an I-V tester, wherein said I-V tester is disposed to measure cell current output, voltage, shunt resistance, series resistance, conversion efficiency and fill factor, wherein said DUT is appropriately binned, according to the criteria of a DUT manufacturer.

23. The shunt defect detection device of claim 1, wherein said DUT is automatically transferred to a pass bin, an uncertain bin, a fail bin, or a further testing bin according to said output status.

* * * * *